(12) United States Patent
Gutman et al.

(10) Patent No.: US 8,021,149 B2
(45) Date of Patent: Sep. 20, 2011

(54) APPARATUS AND METHOD FOR REPLICATING MANDIBULAR MOVEMENT

(75) Inventors: Yevsey Gutman, Minneapolis, MN (US); John Joseph Keller, Anoka, MN (US)

(73) Assignee: Gnath Tech Dental Systems, LLC, Anoka, MN (US)

( * ) Notice: Subject to any disclaimer, the term of this patent is extended or adjusted under 35 U.S.C. 154(b) by 410 days.

(21) Appl. No.: 12/105,249

(22) Filed: Apr. 17, 2008

(65) Prior Publication Data

US 2008/0261169 A1      Oct. 23, 2008

Related U.S. Application Data

(60) Provisional application No. 60/912,299, filed on Apr. 17, 2007.

(51) Int. Cl.
*A61C 19/04* (2006.01)

(52) U.S. Cl. ............... 433/69; 433/54; 433/57; 433/68; 433/229

(58) Field of Classification Search .............. 433/52–69; 434/264; 33/511–514

See application file for complete search history.

(56) References Cited

U.S. PATENT DOCUMENTS

| | | |
|---|---|---|
| 1,848,267 A | 3/1932 | Perkins |
| 1,989,367 A | 1/1935 | Keeney |
| 2,043,394 A | 6/1936 | Keith |
| 2,235,524 A | 3/1941 | Lentz |
| 2,258,473 A | 10/1941 | Scott |
| 2,608,761 A | 9/1952 | Scott |
| 2,621,407 A | 12/1952 | Schlesinger |
| 2,701,915 A | 2/1955 | Page |
| 2,713,721 A | 7/1955 | Page |
| 2,797,483 A | 7/1957 | Lisowski |
| 2,959,857 A | 11/1960 | Stoll |
| 3,160,955 A | 12/1964 | Pietro |
| 3,409,986 A | 11/1968 | Freeman |
| 3,423,834 A | 1/1969 | Irish |
| 4,014,097 A | 3/1977 | Pameijer |
| 4,047,302 A | 9/1977 | Cheythey |
| 4,204,326 A | 5/1980 | Dimeff |
| 4,265,620 A | 5/1981 | Moro et al. |
| 4,279,595 A | 7/1981 | Della Croce |
| 4,292,026 A | 9/1981 | Yokota |
| 4,330,276 A * | 5/1982 | Becker et al. .................. 433/69 |
| 4,354,836 A * | 10/1982 | Santoni ......................... 433/43 |
| 4,391,589 A | 7/1983 | Monfredo et al. |
| 4,417,873 A | 11/1983 | Kulas |

(Continued)

FOREIGN PATENT DOCUMENTS

EP      1 004 281 A2     5/2000

(Continued)

*Primary Examiner* — Cris L Rodriguez
*Assistant Examiner* — Edward Moran
(74) *Attorney, Agent, or Firm* — DuFault Law Firm, P.C.; Dustin R. DuFault (57) ABSTRACT

An apparatus to replicate and analyze movement of a mandible relative to a maxilla with dental casts thereof includes a base frame, an arm connected to the base frame and a suspension assembly positionable by a plurality of electro-mechanical actuators. The arm connects to the base frame and supports the dental cast of the maxilla in a fixed position relative to the base frame. The suspension assembly, having opposing first and second sides, supports the dental cast of the mandible in working relation to the dental cast of the maxilla. The plurality of actuators each selectively impart movement to the sides of the suspension assembly such that the movement of the mandible obtained during a recording process can be replicated on the apparatus in real time.

14 Claims, 5 Drawing Sheets

U.S. PATENT DOCUMENTS

| | | |
|---|---|---|
| 4,447,207 A | 5/1984 | Kataoka et al. |
| 4,468,198 A | 8/1984 | Kataoka et al. |
| 4,501,556 A | 2/1985 | Zelnigher |
| 4,504,226 A | 3/1985 | Gordon |
| 4,624,639 A | 11/1986 | Wong |
| 4,668,189 A | 5/1987 | Levandoski |
| 4,773,854 A | 9/1988 | Weber |
| 5,006,065 A * | 4/1991 | Waysenson ............. 433/63 |
| 5,160,262 A | 11/1992 | Alpern et al. |
| 5,334,017 A | 8/1994 | Lang et al. |
| 5,340,309 A | 8/1994 | Robertson |
| 5,605,456 A | 2/1997 | Young |
| 5,632,619 A | 5/1997 | Polz |
| 5,743,732 A | 4/1998 | Watson |
| 5,807,102 A | 9/1998 | Lang et al. |
| 6,015,291 A | 1/2000 | Cramer et al. |
| 6,024,563 A | 2/2000 | Shiraishi et al. |
| 6,120,290 A * | 9/2000 | Fukushima et al. ............ 433/69 |
| 6,223,648 B1 | 5/2001 | Erickson |
| 6,511,318 B2 | 1/2003 | Kim |
| 6,616,449 B1 | 9/2003 | Rocher |
| 2006/0072799 A1 | 4/2006 | McLain |
| 2009/0035739 A1* | 2/2009 | Alemzadeh ................... 434/264 |

FOREIGN PATENT DOCUMENTS

JP    02001112743 A    4/2001

* cited by examiner

APPARATUS AND METHOD FOR REPLICATING MANDIBULAR MOVEMENT

CROSS-REFERENCE TO RELATED APPLICATION(S)

This application claims the benefit of U.S. Provisional Patent Application No. 60/912,299 entitled APPARATUS TO REPLICATE LOWER JAW MOVEMENT IN REAL TIME AND METHODS OF USING SAME filed on 17 Apr. 2007, which is hereby incorporated herein by reference.

BACKGROUND OF INVENTION

The present invention generally relates to dental restorative or corrective work. In particular, the present invention relates to an apparatus for replicating mandibulary movement for use in dental restorative and corrective work.

In restorative dentistry, it is critical that proper occlusion between the upper and lower jaws of a patient be established to maximize comfort of the patient during mastication. In corrective dentistry, especially that concerning those suffering from tempormandibular joint syndrome, a full and complete understanding of a specific patient's jaw movement is needed in order to properly diagnose and implement a treatment plan for the patient. Improper occlusion may not only lead to the discomfort of the patient while chewing, but may also contribute to other chronic debilitating affects, including improperly aligned condyles. Because such occlusion of the upper and lower jaws is so closely related to condylar movement about the tempormandibular joint, a complete understanding of such movement is essential in making gnathological determinations factors related to the dental restorative or corrective work.

Occlusal motion, though, is quite complex. While a dominant factor of occlusal motion includes pivotal movement of the lower jaw about a hinge axis through the temporomandibular joint ("TMJ"), other factors contributing to the movement include torsional and linear movement of the lower jaw. Such movement can be characterized as having factors relating to pitch, yaw and roll, as well as linear movement transverse to the condylar axis. It has therefore been quite difficult to not only record mandibular movement, but also precisely replicating such movement within precise tolerances.

There exist in the art a wide variety of devices which have attempted to replicate, using dental casts, the occlusal relationship between the upper and lower jaw. In the prior art, incremental changes in the attempts to replicate the occlusal relationship can be observed. Early examples include those suggested by U.S. Pat. No. 1,848,267, 1,989,367 and 2,043,394. These devices, known as dental articulators, had several inherent shortcomings, primarily the ease of use and overall accuracy. None of these examples permitted pivotal movement of one cast relative to the other. Eventually, semi-adjustable and adjustable articulators appeared, including those as suggested by U.S. Pat. No. 3,218,716; 3,431,649; and 4,034,475. These examples, however, had inherent shortcomings in that only simple pivotal motion of either jaw relative to the other could be observed. A precise means of replicating mandibular movement was still needed in the area of dentistry, especially to replicate mandibular movement in real time.

The prior art also includes examples of devices which attempted to mimic mandibular movement. These examples, however, have been found to be unreliable in producing successful results, so there still remains a need to precisely and accurately replicate mandibular movement.

BRIEF SUMMARY OF INVENTION

The present invention includes an apparatus to replicate in real time mandibular movement using dental casts of an upper jaw portion and a lower jaw portion obtained from a patient. The apparatus includes a base frame for supporting an arm to hold the dental cast of the upper jaw, a positionable suspension assembly supporting a platform to hold the dental cast of the lower jaw, and a plurality of actuators for imparting movement to the suspension assembly. The suspension assembly includes first and second opposing struts which connect to the platform in such a manner so as to represent a hinge axis along a tempormandibular joint of the patient. Each actuator connects to the struts through a series of linkages. A computer, using data obtained during a process of recording mandibular movement of the patient, selectively activates each actuator to synchronously impart movement to each strut. First and second actuators impart elevation to a lower portion of each strut. Third and fourth actuators impart translational movement to a middle portion of each strut. A fifth actuator imparts lateral movement to an upper portion of one of the struts. Each of the aforementioned actuators represent five active degrees of freedom in displacement mode. A sixth passive degree of freedom is imparted by a sixth actuator which applies force to a rearward portion of the platform. The passive degree of freedom represents an approach motion between the upper and lower jaw about the tempormandibular joint. The dental cast of the lower jaw is thereby positionable within six degrees of freedom in a reference or coordinate system.

DETAILED DESCRIPTION

Figure 1:
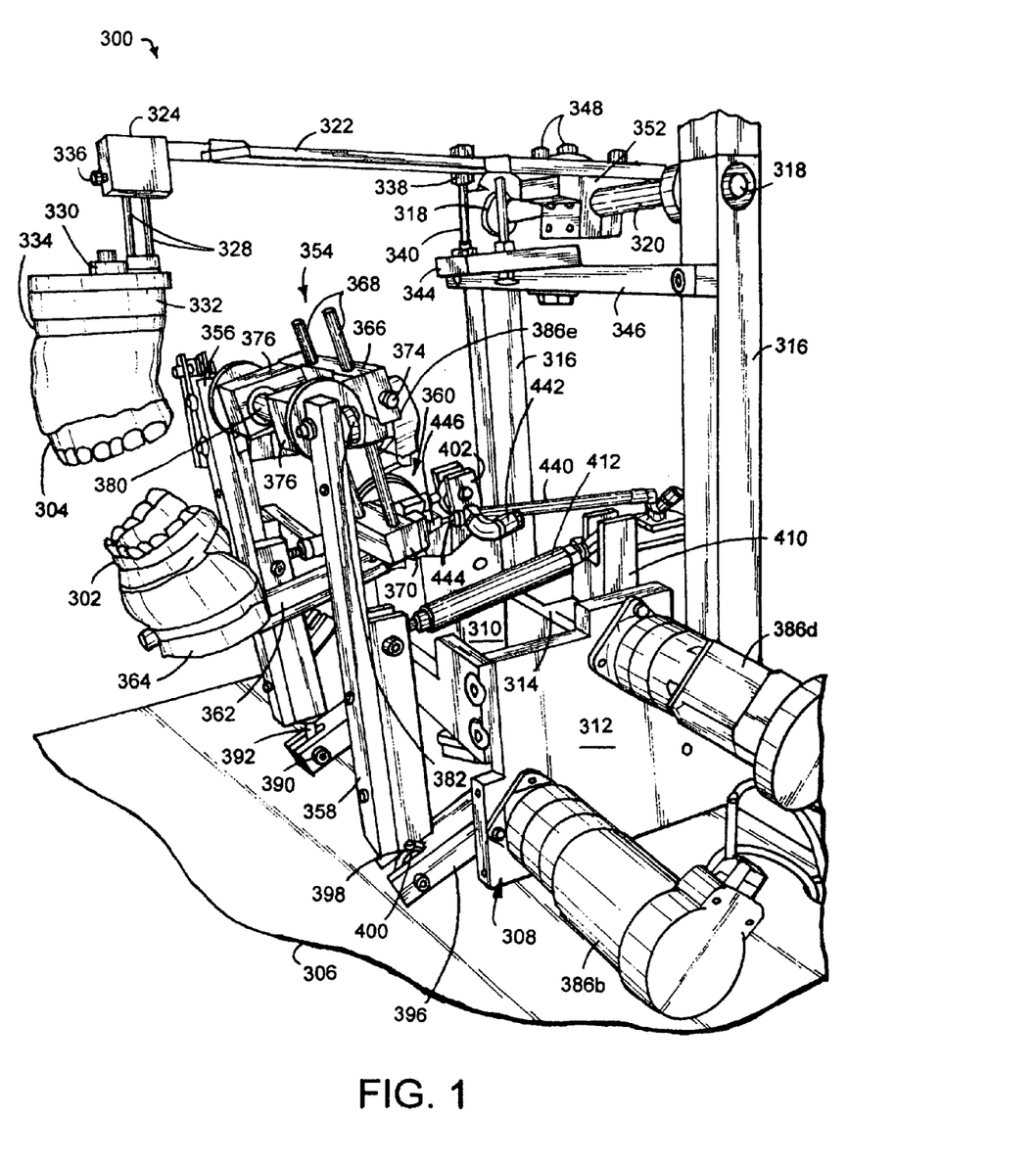
FIG. 1 is a right-hand perspective view of a replicating apparatus of the present invention.
Figure 2:
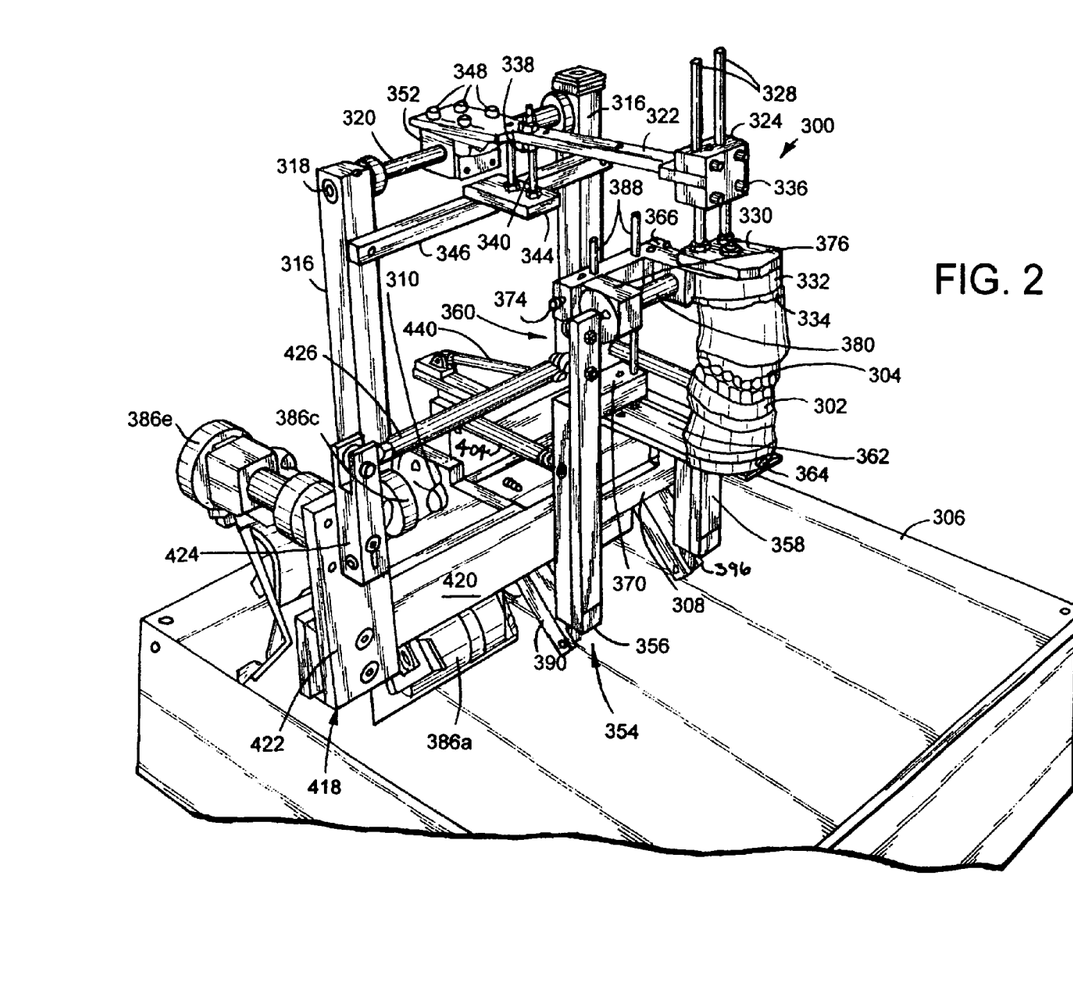
FIG. 2 is a left-hand perspective view of the replication apparatus of the present invention.

An apparatus to replicate mandibular movement in real time is generally indicated at 300 in FIGS. 1 and 2. Generally, the apparatus includes a computer controlled mechanical system driven by information derived from a recording device to create, amongst other things, exact duplication of movement between a dental cast of the lower jaw 302 relative to a dental cast of the upper jaw 304 in real time.

As illustrated in the accompanying Figures, the replicator apparatus 300 is either supported by or mountable to a work surface 306. The replicator 300 includes a base frame 308 having opposing first and second side walls, 310 and 312 respectively, joined together by a rear wall 314. The sidewalls 310, 312 provide the main support for the apparatus 300 and are engageable with the work surface 306.

To support the dental cast of the upper jaw 304, the apparatus 300 includes vertically extending post members 316 attached to opposing ends of the rear wall 314. Terminal upper ends of the post members 316 each contain bearings 318 mounted therein for supporting a pivotal shaft 320. The shaft 320 supports a proximal end of a swing arm 322 which is positionable between a working and non-working position (not shown). Attached to a terminal end of the swing arm 322 is a mounting block 324 having a pair of through-bores for receiving rods 328 attached to a mounting bracket 330. The mounting bracket 330 includes a magnetic base 332 for accepting a corresponding mateable base 334 to which is attached the dental cast of the upper jaw 304. The position of the mounting bracket 330 relative to the mounting block 324 is adjustable by sliding the rods 328 through the mounting block 324. Set screws 336 permit frictional engagement of the rods 328 with the mounting block 324 when the desired position of the mounting bracket 330, or the dental cast 304, is achieved. Further, the angle at which the swing arm 322 rests relative to the work surface 306 can be adjusted by positioning a threaded burr 338 on a threaded bolt 340 which extends through an aperture in the swing arm 322. The threaded bolt 340 and swing arm 322 attach to a platform 344 supported by a cross beam 346 having terminal ends attached to each post 316. The swing arm 322 rests upon the threaded burr 338, and by rotating the burr 338, the swing arm 322 can be raised or lowered to the desired position. The swing arm 322 is also positionable transverse to the shaft 320. Bolts 348 dispose through slotted apertures contained within the swing arm 322 and threadably engage a second mounting block 352 fixedly attached to the shaft 320.

Figure 3:
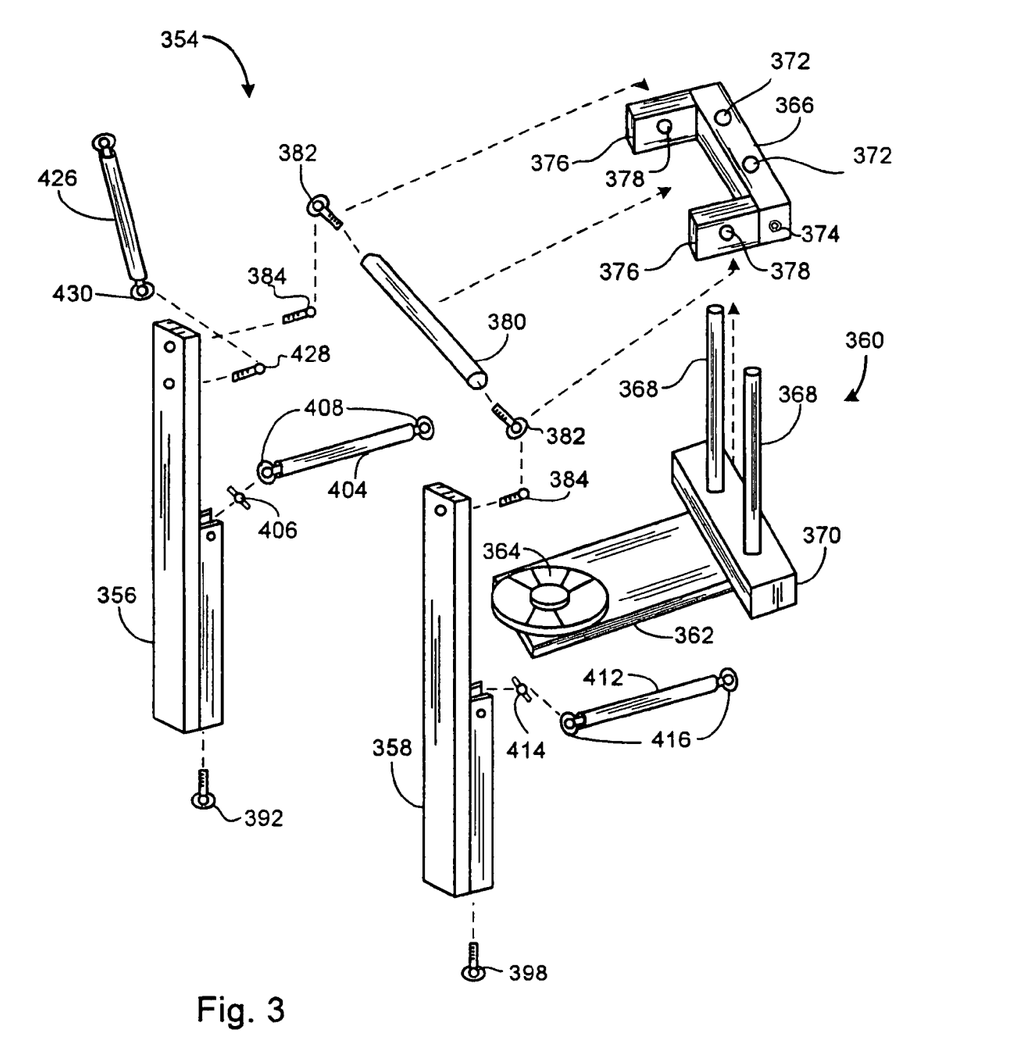
FIG. 3 is an exploded perspective view of a suspension assembly of the present invention.

To support the dental cast of the lower jaw 302, and to provide three-dimensional positioning of the dental cast of the lower jaw 302 relative to the stationary dental cast of the upper jaw 304, a suspension system is provided 354. As illustrated in FIG. 3, the suspension system 354 generally includes first and second spaced apart struts, 356 and 358 respectively, to which is mounted a support assembly 360. The support assembly 360 includes a platform 362 for supporting a magnetic base 364 attached to the dental cast of the lower jaw 302. The platform 362 is suspended from a yoke 366 by rods 368 extending from a connecting block 370 to which is attached the platform 362. Each rod 368 slidably disposes within a corresponding aperture 372 contained within the yoke 366. The position of the platform 362 relative to the yoke 366 is adjustable by allowing each rod 368 to slide within the respective aperture until the desired position of the platform is achieved, at which time set screws 374 frictionally engage the rods 368 to the yoke 366. To attach the support assembly 360 to the struts 356, 358, first and second blocks 376 extend from the yoke 366, each containing an aperture 378 for receiving a shaft 380. Threadably engaged to each end of the shaft 380 are rod end bearings 382 for receiving a ball joint 384 attached to an upper portion of each strut 356, 358. The ball joints 384 therefore permit fluid positioning of the support assembly 360 through the displacement of each strut 356, 358.

The suspension assembly 354 is positionable within six degrees of freedom in a reference or coordinate system by means of articulators and linkages connected to the frame 308 and the suspension assembly 354. The six degrees of freedom are broken down into two groups, including five active degrees of freedom and one passive degree of freedom. Providing the five active degrees of freedom are angular actuators 386. Referring again to FIGS. 1 and 2, each angular actuator 386 is preferably a servomotor. Servomotor 386a attaches to the first sidewall 310 and connects to a lower portion of the first strut 356 by means of a linkage 390. Such attachment of the linkage 390 to the strut 356 is accomplished by means of a rod end bearing 392 and mateable ball joint 394. The rod end bearing 392 attaches to the strut 356 and the ball joint 394 attaches to the linkage 390. However, it is well within the scope of the present invention to attach the rod end bearing 392 to the linkage 390 and the ball joint 384 to the strut 356. When selectively activated, the servomotor 386a pivots the linkage 390 in either a clockwise or counter-clockwise relation, which in turn imparts a vertical movement to the lower portion of the first strut 356 at the point of attachment, either upwardly or downwardly. A corresponding servomotor 386b attached to the second side wall 312 provides similar vertical movement to a lower portion of the second strut 358 when activated. As such, servomotor 386b connects to the second strut 358 by means of linkage 396, rod end bearing 398 and ball joint 400, in much the same manner that servomotor 386a connects to the first strut 356.

Also attached to the first side wall 310 is servomotor 386c. Servomotor 386c connects to the first strut 356 proximately midway along the length of the strut. The servomotor connects to the strut 356 by means of a linkage 402 and connecting arm 404. Both the linkage 402 and the strut 356 each include a ball joint 406 for journaling with corresponding rod end bearings 408 attached to terminal ends of the connecting arm 404. When activated, the servomotor 386c pivots the linkage 402 in either a clockwise or counterclockwise relation, which in turn imparts a translational movement, either rearward or forward, to the first strut 356. A corresponding servomotor 386d attached to the second side wall 312 provides similar translational movement to a middle portion of the second strut 358 when activated. As such, the servomotor 386d connects to the second strut 358 by means of linkage 410, connecting arm 412 with rod end bearings 416 and ball joints 414, in much the same manner that servomotor 386c connects to the first strut 356.

To laterally position the suspension system 354, servomotor 386e is provided. Servomotor 386e connects to the frame 308 by an "L"-shaped bracket 418 having a first leg 420 attached to the frame 308 and a second leg 422 for attaching the servomotor 386e thereto. Servomotor 386e is positioned substantially orthogonal to the other servomotors 386a through 386d and connects to an upper portion of the first strut 356 by means of a linkage 424 and connecting arm 426. Both the linkage 424 and the strut 356 each include a ball joint 428 for journaling with corresponding rod end bearings 430 attached to terminal ends of the connecting arm 426. When activated, the servomotor 386e pivots the linkage 424 in either a clockwise or counterclockwise relation, which in turn imparts a lateral movement, either left or right, to the upper portion of the first strut 356.

Providing the sixth passive degree of freedom is a linear actuator 440 mounted to the rear wall 314 of the frame 308 and connected to the connecting block 370 attached to the platform 362. The linear actuator 440 provides a constant force to the support assembly 360, and therefore preferably includes a pneumatic cylinder. However, the amount of force can be controlled to increase or decrease the amount of pressure to simulate chewing conditions. A port 442 allows introduction of air into the cylinder 440, which in turn forces a piston against the connecting block 370 of the support assembly 360. To provide for constant force throughout all movements of the support assembly 360, a distal end of the cylinder 440 includes a ball joint 444 which mateably engages a corresponding housing 446 attached to the connecting block 370.

As described, the servomotors, 368a through 368e, connect to the suspension assembly 354 and deliver five active degrees of freedom along a hinge line of an imaginary tempormandibular joint. This imaginary line extends through the center of each ball joint 384 connecting the platform assembly 360 to each strut 356, 358. The ball joints 384 represent a pivot axis for the hinge, or an axis around which the platform assembly, and subsequently the dental cast of the lower jaw 302, pivots. The angle of rotation about this hinge is the sixth degree of freedom, and is referred to herein as the passive degree of freedom. The passive degree of freedom represents an approach motion between both jaws about the tempormandibular joint hinge. The passive degree of freedom is controlled in force mode, as compared to the other five active degrees of freedom which are controlled in displacement mode by the servomotors. The difference between force mode and displacement mode is that the active degrees of freedom effectively deliver the tempormandibular joint hinge into the desired position and orientation, while the passive degree of freedom in force mode maintains constant, or any desired force, on the platform 362 to achieve proper contact between upper and lower teeth of the respective dental casts 302, 304. Thus, the passive degree of freedom is controlled by the pneumatic cylinder 440 to provide a selected force to simulate the forces of working, or rather chewing, teeth. Preferably, the amount of pressure maintained on the pneumatic cylinder rangers from about 1 psig to 3 psig. However depending upon the effective piston area, or the application process, the force can be as high as 20 psig.

To provide a realistic motion of the lower jaw dental cast 302 relative to upper jaw dental cast 304, a synchronized motion of all the active degrees of freedom must be simultaneously controlled in real time. Any time delay creates an error in trajectory as well as wrong positioning of the lower jaw dental cast 302 versus the upper jaw dental cast 304. Positioning of the suspension system 354 is controlled by the servomotors 386a through 386e, which each include optical encoders (not shown) as a source of the feedback information. This network of motors and linkages represents a system having multiple degrees of freedom with high cross-coupling effects between input parameters, such as command signals, to the servomotors 386, or motor shaft positions of the servomotors, to provide true positioning of the lower jaw dental cast 302 versus the upper jaw dental cast 304. This is achieved through a closed loop control of the lower jaw in real time using both Direct and Inverse Kinematic Transformations, which are performed by a computer 448 running a software application and based upon positional data received during the recording process. It should be noted that use of the apparatus 300 of the present invention is not meant to be limited to any particular recording process, especially any process which is capable of recording or obtaining mandibular movement in an electronically stored format. However, the preferred mode of recording is that as described in concurrently filed U.S. application Ser. No. 12/105,246 entitled APPARATUS AND METHOD FOR RECORDING MANDIBULAR MOVEMENT, the entirety of which is incorporated herein by reference.

As part of the set-up prior to using the apparatus 300, it is necessary that an initial reference position be set to establish the proper relationship between the dental casts, 302, 304 when mounted on their respective bases 364, 332. In order to do so, several calibration devices are used. The calibration devices ensure the user that the integrity of information transferred from the recorder 452 to the replicator 300 is not lost and both jaws will be placed into replicator with the proper relative alignment.

Figure 4:
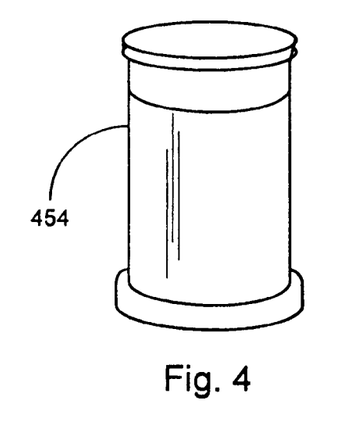
FIG. 4 is a perspective view of a calibrating bar as used in accordance with the present invention.

To properly adjust the swing arm 322 and platform assembly 360 to receive the dental casts 302, 304, two parameters are obtained during the recording process, namely the vertical and horizontal positioning of the platform relative to the center points of the ball joints or hinge axis. The vertical positioning includes the distance as measured between two imaginary planes substantially horizontal to the work surface, one passing through the condylar ball joints 384 and the other consisting of a plane through the platform 362. The horizontal positioning includes the distance between two imaginary planes substantially orthogonal to the work surface, one passing through the condylar ball joints 384 and the other passing through the center of each magnetic base member 332, 364 respectively attached to the swing arm 322 and platform 362. The position of both the platform 362 and the swing arm 322 are then adjusted adjustable as described herein. Upon making the proper adjustments, the dental casts are attached to their respective bases and are brought together to define to the home occlusal position. A calibration bar 454, as illustrated in FIG. 4, used during the setting up of the dental casts 302, 304 is then used to establish the proper distance between each upper base 332 and the lower base 364.

Figure 5:
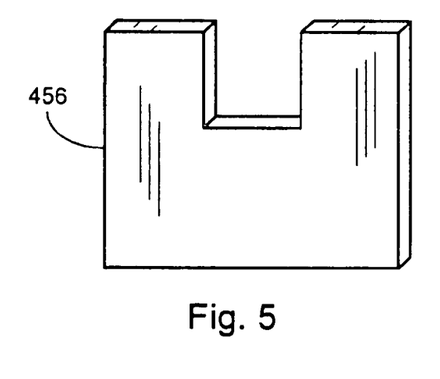
FIG. 5 is a perspective view of a calibrating frame as used in accordance with the present invention.
Figure 6:
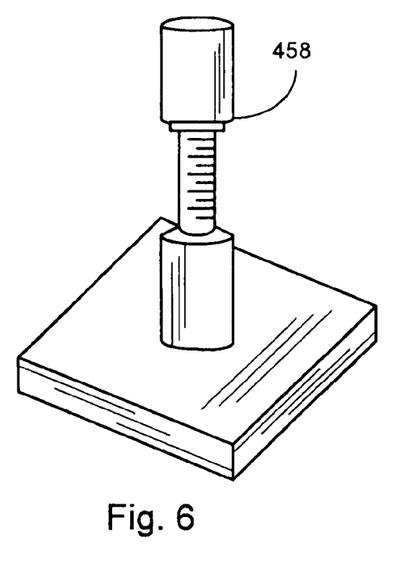
FIG. 6 is a perspective view of an adjusting device as used in accordance with the present invention.

The articulator 300 is then calibrated with the computer 448 to determine the initial reference or home position. With reference to FIGS. 5 through 6, this is accomplished by using a calibration frame 456 and adjustable support device 458. The calibration frame 456 rests upon the works surface 306 and supports the suspension assembly 354 at a fixed position. The adjustable support device is then positioned between the work surface 306 and the platform 362 to provide support to the platform 362. When the calibration frame 456 and adjustable device 458 are in place, the computer 448 zeros out all optical encoders used for feedback to control servo loops. Thus, by use of the calibrating frame 456 and adjustable support device 458, the reference or zero position can be calibrated which can be verified and compared with other fixtures. This initial reference position is critical because closed loop control is used around each individual servo motor 386, meaning that the apparatus 300 is controllable in Joint Domain and not TMJ Domain, as is fully described in concurrently filed application previously referenced herein. Joint Domain represents all mechanical joints used by the recording device as a part of the multiple degrees of freedom linkage, while TMJ Domain is associated with coordinates of each center of the condyles and the rotational angle about the axis through each condyle. That type of control requires a transfer function between the Joint Domain and the TMJ Domains, which is performed by a software program within the computer 448 to be performed in real time or in preprocessed mode.

Figure 7:
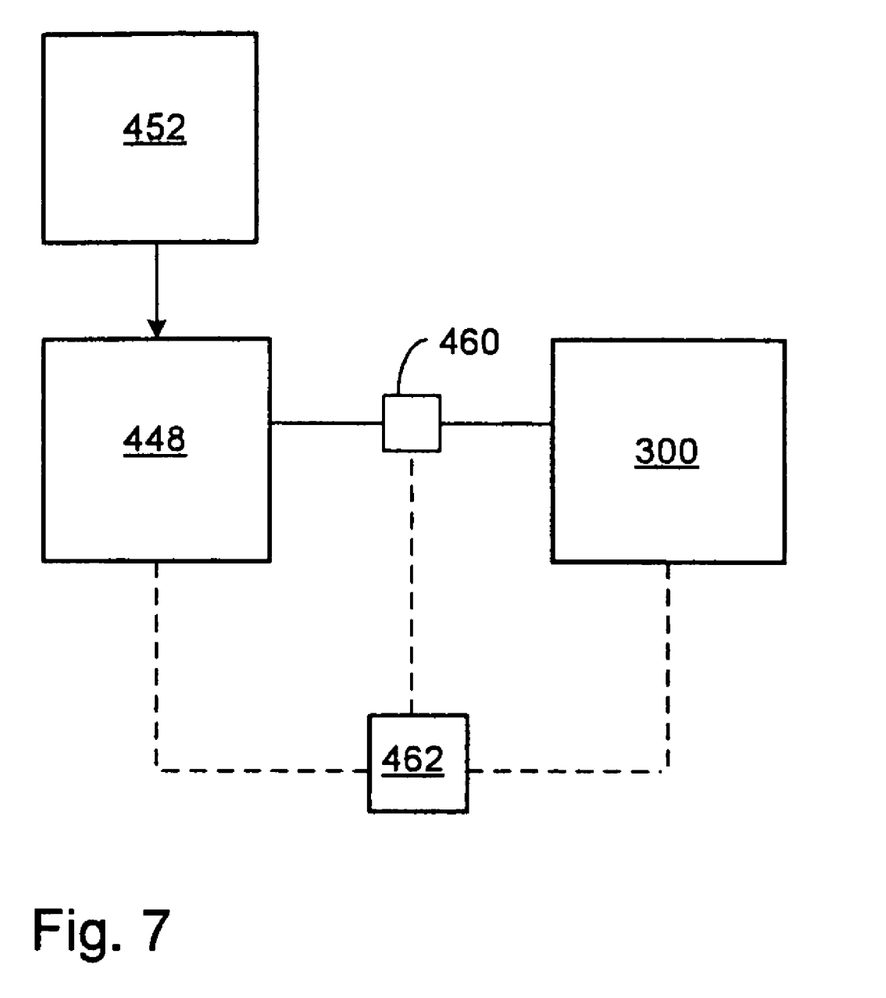
FIG. 7 is a diagram of the present invention showing a general arrangement of components.

The servomotors 386 are controlled by an interface module which is controlled by the computer 448 by a motion interface board. The interface board is preferably includes Model No. DMC-1800 as made commercially available by Galil Motion Control of Rocklin, Calif. As illustrated in FIG. 7, a separate power source 462 runs all of the servomotors 386. Running the software application, the computer 448 selectively and synchronously activates each servomotor 386a through 386e to position the suspension assembly 354 to move the lower dental cast 302 relative to the upper dental cast 304 to accurately replicate the actual movement obtained during the recording process. The upper jaw dental cast 304, attached to the swing arm 322, remains stationary with respect to the replicator 300 and does not move during the replicator process. However, the arm 322 can be preset for any given settings and still perform during replication wherein the computer 448 recalculates command signals to control the servomotors 386a through 386e to follow the desired trajectory from the pre-recorded settings into any the actual settings used during the replication. The swing arm 322 can be pivoted away from the platform assembly 360, whereby the similar dental casts 302, 304 can be removed or replaced if testing on dental casts from the same patient is desired. Because all of the settings are preserved, recalibration of the apparatus 300 is not required. Also, the swing arm 322 is designed to pivot out of place if the force supplied to the lower dental cast 302 is too great, thereby minimizing damage to the dental casts 302, 304, the swing arm 322 or the suspension assembly 354 is such an event should occur.

Although the present invention has been described with reference to preferred embodiments, workers skilled in the art will recognize that changes may be made in form and detail without departing from the spirit and scope of the invention.

The invention claimed is:

1. An apparatus to replicate and analyze movement of a mandible relative to a maxilla with dental casts thereof, the apparatus comprising:
    a base frame;
    an arm connected to the base frame for supporting the dental cast of the maxilla in a fixed position relative to the base frame;
    a suspension assembly to support the dental cast of the mandible in working relation to the dental cast of the maxilla, the suspension assembly including opposing first and second sides, a platform for supporting the dental cast of the mandible, and a yoke member supporting the platform, the yoke member having a first side corresponding with the first side of the suspension assembly and a second side corresponding with the second side of the suspension assembly;
    a first positionable strut attached to the first side of the yoke member;
    a second positionable strut attached to the second side of the yoke member, the platform positionably disposed between the first and second struts, wherein the attachment of the yoke member to the struts defines a pivoting axis of the suspension assembly, the pivoting axis positioned above the platform;
    a first actuator to impart lateral movement upon the suspension assembly;
    a second actuator to impart forward or rearward movement to the first side of the suspension assembly;
    a third actuator to impart forward or rearward movement to the second side of the suspension assembly;
    a fourth actuator to elevate or lower the first side of the suspension assembly; and
    a fifth actuator to elevate or lower the second side of the suspension assembly, whereby activating each actuator to impart said respective movement, the suspension assembly is positionable to replicate movement of the mandible relative to the maxilla;
    wherein the first actuator connects to either the first strut or the second strut, wherein the second and fourth actuators connect to the first strut, wherein the third and fifth actuators connect to the second strut, whereupon activating each actuator the struts are manipulated to position the platform to replicate three-dimensional movement of the mandible relative to the maxilla.

2. The apparatus of claim 1 and further comprising a piston attached to the base frame and the suspension assembly to impart a substantially constant force onto the suspension assembly.

3. An apparatus to replicate movement of a lower jaw of a patient relative to the upper jaw, the apparatus comprising:
    a base frame;
    an arm connected to the base frame for supporting a dental cast of the upper jaw in a fixed position relative to the base frame;
    a positionable platform for supporting a dental cast of the lower jaw in working relation to the dental cast of the upper jaw;
    a first moveable strut connected of the platform;
    a second moveable strut connected to the platform opposite the first strut, the platform positionable between the first strut and the second strut;
    a first actuator to impart lateral movement onto either the first strut or the second strut;
    a second actuator to impart forward or rearward movement to the first strut;
    a third actuator to elevate or lower the first strut;
    a fourth actuator to impart forward or rearward movement to the second strut; and
    a fifth actuator to elevate or lower the second strut, whereupon activating each actuator to impart said movement to the respective strut, the first strut and the second strut impart movement to the platform to reproduce movement of the lower jaw with respect to the upper jaw.

4. The apparatus of claim 3 and further comprising a sixth actuator attached to the base frame and connected to a rearward portion of the platform, the sixth actuator providing a substantially constant force onto the rearward portion of the platform.

5. The apparatus of claim 3 wherein the first actuator connects to the base frame and an upper portion of either the first strut or the second strut, wherein the second actuator connects to the base frame and a mid portion of the first strut, wherein the third actuator connects to the base frame and a lower portion of the first strut, wherein the fourth actuator connects to the base frame and a mid portion of the second strut, and wherein the fifth actuator connects to the base frame and a lower portion of the second strut.

6. The apparatus of claim 5 wherein a rod end bearing connects each of the actuators to the respective strut.

7. The apparatus of claim 3 and further comprising a yoke member, the platform suspended from the yoke member between the first strut and the second strut, the yoke member including first and second opposing ends, wherein the first end pivotally attaches to the first strut and the second end pivotally attaches to the second strut.

8. The apparatus of claim 7 wherein the first end of the yoke member pivotally attaches to the upper portion of the first strut, and wherein the second end of the yoke member pivotally attaches to the upper portion of the second strut, wherein the attachment of the yoke member to the struts defines a pivoting axis of the suspension assembly, the pivoting axis positioned above the platform.

9. An apparatus to replicate and analyze movement of a mandible relative to a maxilla with dental casts thereof, the apparatus comprising:
    a base frame;
    an arm pivotally connected to the base frame for supporting the dental cast of the maxilla in a fixed position;
    first and second spaced-apart upright struts;
    a yoke member disposed between each strut having a first side pivotally attached to the first strut and a second side pivotally attached to the second strut, the pivotal attachment of the yoke to each strut defining a pivot axis;

a plurality of actuators connected to the base frame to impart movement onto the first and second struts to manipulate the position of the yoke member, the plurality of actuators including:
- a first actuator attached to the base frame, the first actuator imparting through a linkage lateral movement to the first strut or the second strut;
- a second actuator attached to the base frame, the second actuator linked to the first strut to impart forward or rearward movement to the first strut;
- a third actuator attached to the base frame, the third actuator linked to the first strut to elevate or lower the first strut;
- a fourth actuator attached to the base frame, the fourth actuator linked to the second strut to impart forward or rearward movement to the second strut;
- a fifth actuator attached to the base frame, the fifth actuator linked to the second strut to lower or raise the second strut; and a platform suspended from the yoke member to support the dental cast of the mandible in working relation to the dental cast of the maxilla, wherein the pivot axis is located above the platform, wherein activating the the plurality of actuators the platform is positionable to replicate three-dimensional movement of the dental cast of the mandible relative to the dental cast of the maxilla.

10. The apparatus of claim 9 and further comprising a sixth actuator for providing a controlled moment about the pivot axis during movement of the platform to simulate chewing conditions.

11. The apparatus of claim 10 wherein the sixth actuator comprises an air compressed actuator connected to the platform applying a near constant force between 1 and 20 psig.

12. The apparatus of claim 11 wherein the sixth actuator applies a near constant force of between 1 and 3 psig.

13. The apparatus of claim 3 wherein the platform is disposed between the first and second struts.

14. The apparatus of claim 4 wherein the sixth actuator comprises an air compressed actuator, the air compressed actuator providing a sixth degree of freedom mimicking chewing.

* * * * *